(12) United States Patent
Shih

(10) Patent No.: US 11,124,449 B2
(45) Date of Patent: Sep. 21, 2021

(54) FABRICATION AND APPLICATIONS OF MULTIPLE SIDE-WINDOW, SIDE-FIRING OPTICAL FIBER

(71) Applicant: University of Houston System, Houston, TX (US)

(72) Inventor: Wei-Chuan Shih, Houston, TX (US)

(73) Assignee: University of Houston System, Houston, TX (US)

( * ) Notice: Subject to any disclaimer, the term of this patent is extended or adjusted under 35 U.S.C. 154(b) by 392 days.

(21) Appl. No.: 16/326,986

(22) PCT Filed: Aug. 31, 2017

(86) PCT No.: PCT/US2017/049687
§ 371 (c)(1),
(2) Date: Feb. 21, 2019

(87) PCT Pub. No.: WO2018/045206
PCT Pub. Date: Mar. 8, 2018

(65) Prior Publication Data
US 2020/0123053 A1 Apr. 23, 2020

Related U.S. Application Data

(60) Provisional application No. 62/381,730, filed on Aug. 31, 2016.

(51) Int. Cl.
*C03C 25/6208* (2018.01)
*C03C 25/106* (2018.01)
*C03C 25/68* (2006.01)
*F21V 8/00* (2006.01)

(52) U.S. Cl.
CPC ...... *C03C 25/6208* (2018.01); *C03C 25/1063* (2018.01); *C03C 25/68* (2013.01); *G02B 6/001* (2013.01)

(58) Field of Classification Search
CPC ............. C03C 25/6208; C03C 25/005; C03B 37/01234; C03B 37/01228; C03B 37/10; G02B 6/001; G02B 6/02071; G02B 6/02066; G02B 6/0229; G02B 6/02314; G02B 6/02357; G02B 6/02361; G02B 6/02376; G02B 6/02352
See application file for complete search history.

(56) References Cited

U.S. PATENT DOCUMENTS

| | | | | |
|---|---|---|---|---|
| 5,321,257 A | * | 6/1994 | Danisch | G02B 6/02066 250/227.16 |
| 5,411,566 A | * | 5/1995 | Poole | C03B 37/15 385/28 |
| 5,432,876 A | * | 7/1995 | Appeldorn | G02B 6/001 362/554 |
| 5,858,799 A | | 1/1999 | Yee et al. | |
| 6,408,118 B1 | * | 6/2002 | Ahuja | G02B 6/02 385/123 |
| 6,975,792 B1 | * | 12/2005 | Goldberg | G02B 6/4202 385/15 |
| 2005/0074207 A1 | * | 4/2005 | Shioda | G02B 6/122 385/31 |
| 2005/0165315 A1 | | 7/2005 | Zuluaga et al. | |
| 2009/0287200 A1 | | 11/2009 | Hanley et al. | |
| 2011/0038580 A1 | | 2/2011 | Griffin | |
| 2018/0299614 A1 | * | 10/2018 | Schwagmeier | G02B 6/001 |

FOREIGN PATENT DOCUMENTS

WO 2009/066969 5/2009

OTHER PUBLICATIONS

Notification of Transmittal of the International Search Report and Written Opinion of the International Searching Authority—The Korean Patent Office—dated Mar. 16, 2018 for International Application No. PCT/US2017/049687, 13 pages.
Notification of Transmittal of the International Preliminary Report on Patentability containing the Written Opinion of the International Searching Authority—The Korean Patent Office—dated Mar. 16, 2018, mailed by the International Bureau of WIPO on Mar. 14, 2019 for International Application No. PCT/US2017/049687, 10 pages.

* cited by examiner

*Primary Examiner* — Cynthia Szewczyk
(74) *Attorney, Agent, or Firm* — Jackson Walker LLP

(57) ABSTRACT

The present disclosure relates to the fabrication and characterization of an optical fiber capable of firing light virtually from any point along its circumferential surface. The optical fiber is preferably prepared by laser micromachining. In preferred embodiments, laser radiation is focused onto a multimode optical fiber axis, forming a conical-shaped cavity (side window) in the fiber core. Because of the total internal reflection when the laser beam reaches the side window-outside medium interface, the beam is reflected to the side of the optical fiber.

26 Claims, 12 Drawing Sheets

Coupled light beam

Fiber core

FIG. 5
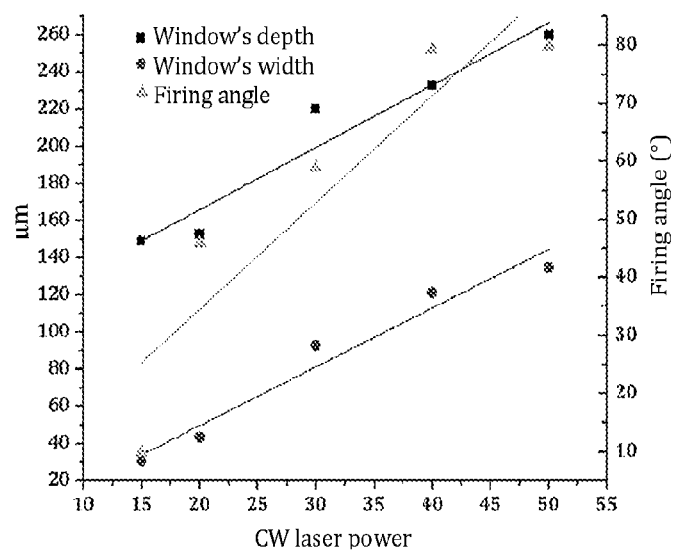
FIG. 6A FIG. 6B
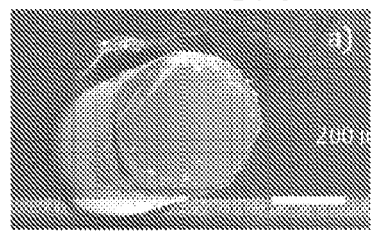 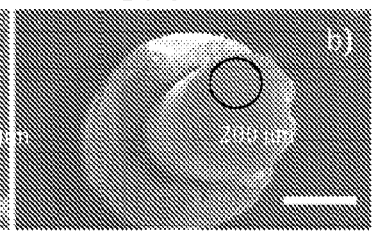
FIG. 6C FIG. 6D
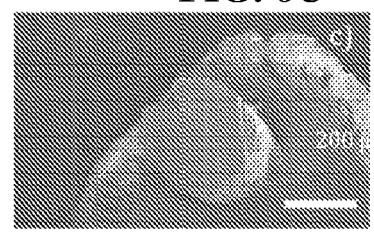 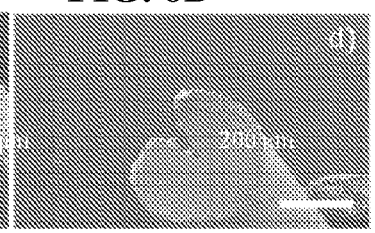

Output light spectra of intact optical fiber sample

Optical fiber sample

FABRICATION AND APPLICATIONS OF MULTIPLE SIDE-WINDOW, SIDE-FIRING OPTICAL FIBER

This application claims priority to U.S. Provisional Patent Application No. 62/381,730, entitled "Fabrication and Applications of Multiple Side-Window, Side-Firing Optical Fiber," filed on Aug. 31, 2016, the entire contents of which are hereby incorporated by reference.

The present invention used in part funds from the National Institute of Health (NIH) ((NIH 1R21NS084301-01A1), National Science Foundation (NSF) CAREER Award (CBET-1151154), and Department of Interior BSEE. The United States Government has certain rights in the invention.

BACKGROUND

This disclosure pertains to the fabrication and applications of an optical fiber, and in particular, to an optical fiber having side windows.

Optical fibers have been developed as a means to guide light of various wavelength and frequency over a long distance. Light is coupled through one end and emitted through another end with minimal loss of energy. Optical fibers have been used widely in numerous biomedical applications based on their frontal light firing design.

SUMMARY

The present disclosure relates broadly to optical fibers. In particular, the present disclosure pertains to multi-point side-firing optical fibers, as well as their methods of fabrication and their uses.

Side emission of optical fiber is typically done via two different methods: a metal reflector or total internal reflection. The former comprises a mirror made of gold alloy or gold coating. The mirror is positioned in front of the polished, flat surface of the fiber distal end to deflect the incoming beam. Even though the metal mirrors have good reflectivity, the heat generated on their surface might pose a serious problem when using in clinical applications. The latter is made possible by polishing the tip of the fiber under an angle so that it frustrates the total internal reflection (TIR) condition of the incoming beams. As a result, light inside the core is deflected to the side. Several side firing optical fiber probes had been fabricated using the latter method's principal. Although side-firing was achieved, the illumination site was still limited at the tip of the fibers. Other types of side firing fibers such as surface-emitting fiber laser and side glowing fiber were also introduced recently, but in terms of output efficiency, they are poor and do not have control over the illumination area. Furthermore, the fabrication methods are complex, time-consuming and cost-ineffective, thus not suitable for mass production or fast prototypes of the devices.

The present disclosure relates to the fabrication and characterization of an optical fiber capable of firing light virtually from any point along its circumferential surface. The optical fiber is preferably prepared by laser micromachining. In preferred embodiments, laser radiation is focused onto a multimode optical fiber axis, forming a conical-shaped cavity (side window) in the fiber core. Because of the total internal reflection when the laser beam reaches the side window-outside medium interface, the beam is reflected to the side of the optical fiber. A single side window on 730 µm fiber can deliver more than 8% of the total coupled light. However, light-firing output from 65 µm optical fiber can be increased to more than 19%. In addition, the fiber also exhibits 3-dimensional light emission by placing side-windows of various orientations on its axis.

In several biomedical applications, a multipoint side firing optical fiber would be very useful. It could provide light distribution to a relatively large and selected region to treat cancer tumors in phototherapy (PT). The side-firing configuration would also help transmit light to difficult-to-reach areas such as diseased tissues located along the sidewall of the tubular structures in the human body, for example, the ureter. Last but not least, it could also be used to give multi-site stimulation in optogenetics as well as fabric display. Recently, together with traditional optical fibers, side-firing fibers have been developed to provide a more precise medical operation.

In addition to providing multi-site light delivery as described, optical fiber sensors can be fabricated on the side windows. Surface plasmon resonance (SPR)-based or localized surface plasmon resonance (LSPR)-based fiber optic sensors have been a subject for research in quantitative detection of various type of chemical, and biological substances. The advantages of an optical fiber based sensor over its bulk counterpart, the Kretschmann configuration, are its small size, and flexibility that can be utilized to use in small area and for remote sensing applications. To fabricate an SPR-based fiber optic, the buffer jacket and cladding are removed along the fiber length or at the tip of the fiber to expose the entire fiber core. Then a thin (nano) layer of gold or silver, or discrete gold or silver nanoparticles, are deposited on it. Previously, in order to create a smooth surface of the fiber core for fabrication of an SPR sensor, physical techniques are applied to remove the jacket and cladding layer, and then the core surface is polished. However, the physical process is not easy, is labor intensive and is time consuming. Another technique is the torching technique, to burn out all the outer layers of fiber optic. This technique is fast and very simple, but with the cost of uncontrollable burn area. Furthermore, because of the 3D structure of the fiber, it is hard to deposit a full layer of metal around the exposed core. Without full coverage of the metal layer, there is a risk in leaking of light at uncovered area which can lead to the reduction of signal intensity. For example, with the deposition of nanoparticles such as nanoporous gold discs (NPGD) on an optical fiber's core, because of the monolithic fabrication method of the NPGD (as seen in FIG. 1), only the central area of the fiber core can be covered by the plasmonic structure. FIG. 2 shows scanning electron microscope (SEM) images showing NPGD fabricated on an optical fiber. The present disclosure provides a new technique to open windows on optical fiber which is fast, simple, and creates a smooth surface for further deposition with full coverage. The present solution replaces the torching technique with a laser cutter tool which can precisely cut in micrometer scale, and thus is ideal to use for opening small windows on fiber optics.

BRIEF DESCRIPTION OF THE DRAWINGS

FIG. 5 shows dimensions of a side window (depth and width) as a function of $CO_2$ laser power.

FIG. 6A shows a SEM image of a cross section of a fiber core after cut with a $CO_2$ laser at a laser power of 10 W.

FIG. 6B shows a SEM image of a cross section of a fiber core after cut with laser power of 20 W.

FIG. 6C shows a SEM image of a cross section of a fiber core after cut with laser power of 30 W.

FIG. 6D shows a SEM image of a cross section of a fiber core after cut with laser power of 40 W.

DETAILED DESCRIPTION OF PREFERRED EMBODIMENTS

Figure 1:
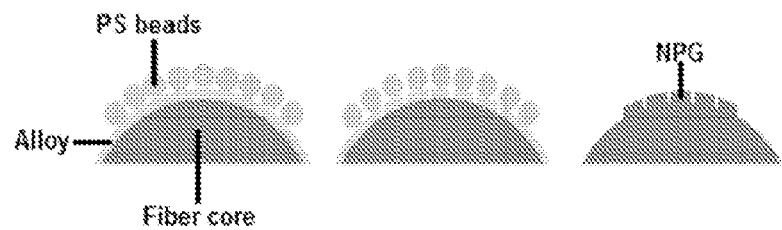
FIG. 1 shows a schematic diagram of a fabrication process for nanoporous gold discs (NPGD) on an optical fiber.
Figure 2:
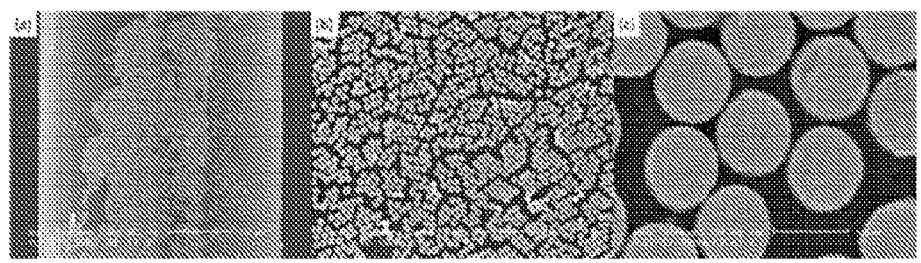
FIG. 2 shows scanning electron microscope (SEM) images showing NPGD fabricated on an optical fiber at (a) low, (b) intermediate, and (c) high resolution.

The present disclosure relates to an optical fiber having multiple side windows allowing for light to be distributed along the length of an optical fiber rather than from its distal end alone. In preferred embodiments, the multi-point side-firing optical fiber is prepared by laser micromachining.

Laser micromachining methods have been studied in depth in making microstructures in various materials, including glass, but none in fabricating side firing windows on optical fiber for multi-point side-firing configuration. In preferred embodiments described herein, a direct writing method is used to modify the optical fiber core, making manipulation of the direction of coupled light possible for side-firing setup. The method may preferably be based on continuous wave (CW) $CO_2$ laser and femtosecond (fs) laser micromachining. Changing and improving the design of the multipoint side-firing optical fiber can be done rapidly and straightforward, hence large quantity production of the fiber and prototyping new fiber designs are also fast. This method can be used to replace other conventional methods to produce side-firing fibers.

In order for light to interact with the external environment along the side of an optical fiber, windows need to be opened. A preferred embodiment relates to a laser micromachining technique to fabricate small windows for the management of light exiting from the side of an optical fiber (aka, "side firing"). In one embodiment, a laser is employed to create a circular "cut" into the fiber core region, creating a round "pit" with the buffer and cladding layers removed and the core partially removed. In this embodiment, a high power carbon dioxide ($CO_2$) pulse laser is focused onto a single point on the fiber to create a dot window (~300 μm in length, ~250 μm in width) with a V-shaped cross section (~133 μm depth). After testing on several samples, using a 473 nm pulse laser to coupe into the fiber, it was confirmed that light exited to the environment from the cut site, but through the opposite side of the cut. The power of exited light is directly proportional to the power of laser used to cut window. For 100% laser power, more than 8% of total light inside the fiber can exit from one window. When cut a second time on the same window, the total power of light exiting reached ~12%. The power of leaked light can still be increased even more up to 20% if the window is cut more time, but it comes with the cost of reduced fiber mechanical strength. A window with depth close or more than half the core diameter (~200 μm) makes the fiber become very fragile. Multiple windows can be placed in closed distance in different radial direction along the fiber length, resulting in a 30 side firing configuration.

In the current disclosure, the terms "window," "side window," "windows" and "side windows" refer to any window, crater, cut, or pit that may be produced in a fiber in accordance with the preferred embodiments disclosed herein, as well as any pattern of multiple windows, craters, cuts, and pits produced in a similar fashion.

The size and placement of the side windows of the optical fiber can be precisely controlled. The amount of light exiting through the window can also be controlled by the laser power and pattern. The side-firing fiber is useful in many applications where it is desirable to have light delivered at more locations other than the end point. For example, this device can serve as a neural probe with multiple light delivery sites for optogenetics stimulation and other light-based techniques. The windowed fiber can also enable applications where sensing and measurement of the local environment is needed. The light that propagates across the laser-cut V-shaped "pit" can interact with gas or fluids residing in that volume and the result of that can be used for detecting the type and concentration of targets species inside that volume. Further, the surface of the laser-cut window can be treated with an additional thin film coating to render surface-based detection such as plasmonic-enhanced sensing. The surface can also be functionalized to capture specific target species external to the fiber.

The multi-point side-firing optical fiber offers unique control over the direction and the output distribution of the light propagating inside the fiber core. Beside potential uses as a light delivery device in biomedical applications, such a fiber can also be used to deliver photo-thermal energy to selectively heat the interior of the shaped memory alloy (SMA) tube to control shape recovery or to harden the superplastic SMA tube. In this manner, a superplastic SMA medical guide-wire could be heated along its long length and hardened to assist the doctor in moving the wire through an occlusion. A heated fiber-SMA tube would also be useful in treating the heart's wall to prevent atrial fibrillation. Additionally, the large area light projection ability of the fiber might be used to trigger light sensitive drugs. It would help speed up the process and avoid the need to reposition the fiber to different regions. The fiber might also have interesting applications in remote sensing technology. Multiple light outputs would allow a large number of optical receivers or detectors to collect energy or data, and retransmit it over a long distance and large area.

Additional key applications for the optical fibers include implantable devices for optogenetics stimulation and sensors in the brain or peripheral neural systems, as well as remote and/or distributed sensors along a single optical fiber. The fiber itself may be any suitable length, including those that are a mile or even longer, with many side windows. Sensor devices could be integrated on such a fiber as a "link." In other applications the fibers may be used in wearable devices. The optical fiber can be easily embedded into garments, clothes, and the like. The fiber sensor can monitor physiological conditions and environmental factors, as well as any other suitable information.

Certain preferred embodiments relate to a method for fabricating a multiple side-window side-firing optical fiber. In this preferred embodiment, a first step may be positioning an optical fiber in a fixed position. The optical fiber is typically made up of an inner silica core, an intermediate cladding layer, and an outer buffer layer having outer side walls along its circumferential surface. A next step may include directing a laser beam from a laser at a selected location on the outer side walls of the optical fiber at which a side window is intended to be placed. The laser beam contacts the optical fiber for a selected period of irradiation time. Next, a crater-shaped side window is produced in the optical fiber using the laser beam. The crater-shaped side window penetrates through the outer buffer layer, the intermediate cladding layer, and at least partially into the inner silica core of the optical fiber. These steps will produce an initial side window in the optical fiber.

To produce multiple side windows in the optical fiber in accordance with a preferred embodiment, the same optical fiber is repositioned in an additional fixed position and a laser beam from the laser is directed at an additional selected location on the outer side walls of the optical fiber at which an additional side window is intended to be placed. Again, the laser beam contacts the optical fiber for an additional selected period of irradiation time, producing an additional crater-shaped side window in the optical fiber. The additional crater-shaped side window also penetrates through the outer buffer layer, the intermediate cladding layer, and at least partially into the inner silica core. These steps may be repeated any number of times to produce a desired number of additional side windows in the optical fiber.

In preferred embodiments, the laser may be any suitable continuous wave or pulsed laser, including but not limited to any suitable gas laser, including but not limited to $CO_2$ or helium-neon lasers, any solid-state laser, including but not limited to yttrium orthovanadate (Nd:YVO4), yttrium lithium fluoride (Nd:YLF) yttrium aluminium garnet (Nd:YAG), or titanium-doped sapphire (Ti-sapphire) lasers, any fiber laser, any semiconductor laser, or the like. Suitable lasers may include femtosecond, picosecond, and nanosecond lasers. In additional preferred embodiments, the laser may be a continuous wave $CO_2$ laser. In further preferred embodiments, the power of the laser and the irradiation time may be adjusted to generate a desired depth of the crater-shaped side windows in the optical fiber. The depth is directly proportional to the power of the laser and the irradiation time. The power of the laser may be selected to be any suitable power and in preferred embodiments may range from about 10-100 W. In additional preferred embodiments, the irradiation time may be any suitable time and may range from about milliseconds to seconds. The resulting depth of the crater-shaped side windows will preferably range from about 1 micron to about 300 microns, depending on the diameter of the optical fiber, which in these preferred embodiments may be about 30 microns to about 1000 microns. In certain preferred embodiments, an additional thin film coating may also be applied before the laser machining step, in between multiple laser machining steps, and after the laser machining step to one or more of the crater-shaped side windows.

Additional preferred embodiments relate to methods of fabricating a multiple side-window side-firing optical fiber that may be of a narrower diameter. In these situations, it may not be desirable to allow the laser beam to produce the entire crater-shaped side window. In these preferred embodiments, the laser beam is used to produce a circular-shaped opening at the selected location in the optical fiber. The circular-shaped opening penetrates through the outer buffer layer without penetrating the intermediate cladding layer or the inner silica core. In a next step, the optical fiber, or at least the portion including the circular-shaped opening, is immersed in a chemical etching solution. The chemical etching solution penetrates through the intermediate cladding layer and at least partially into the inner silica core of the optical fiber to create a crater-shaped side window at the selected location in the optical fiber. In these additional preferred embodiments, the laser may be any suitable laser, including those described above. In further preferred embodiments, the laser may be a pulsed femtosecond laser. The power of the laser and the irradiation time may be adjusted to generate a desired depth of the circular-shaped opening in the optical fiber. The power of the laser may be selected to be any suitable power and in preferred embodiments may range from about 10-100 W. In additional preferred embodiments, the irradiation time may be any suitable time and may range from about milliseconds to seconds. The resulting depth of the crater-shaped side windows will preferably range from about 1 micron to about 300 microns, depending on the diameter of the optical fiber, which in these preferred embodiments may be about 30 microns to about 1000 microns. The chemical etching solution can be any suitable chemical etching solution for optical fibers and is preferably a buffered HF solution. In certain preferred embodiments, an additional thin film coating may also be applied before the laser machining step, before the etching step, and after the etching step to one or more of the crater-shaped side windows.

The multiple side-window side-firing optical fiber can be used in a number of applications. In certain embodiments, the multiple side-window optical fibers are used to provide multiple simultaneous points of light to a region using a single optical fiber. The multiple side-window side-firing optical fiber can be inserted into a desired region. Then, a laser is directed through the multiple side-window side-firing optical fiber. Laser light passes through the distal end of the fiber, and laser light also passes through the outer side walls of the fiber at locations opposite the crater-shaped side windows. This can be carried out in any suitable location. Smaller diameter optical fibers can be inserted into human tissues or other regions in a human or animal subject in order to provide multiple points of light.

In additional embodiments, the multiple side-window side-firing optical fiber can be used to produce surface plasmon resonance (SPR)-based or localized surface plasmon resonance (LSPR)-based fiber optic sensors. As already discussed, crater-shaped side windows are produced in the optical fiber, where the buffer jacket and cladding have been removed to expose the fiber core. Then a nano layer of gold or silver, or discrete nanoparticles, are deposited on the exposed core at the location of the side window to create the SPR or LSPR sensor.

Example 1

Figure 3A:
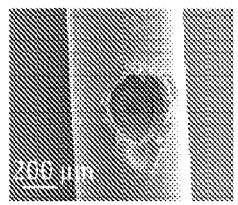
FIG. 3A shows a SEM image of a top view of a light window fabricated by a 50 W continuous wave laser in an optical fiber with buffer and cladding layers intact.
Figure 3B:
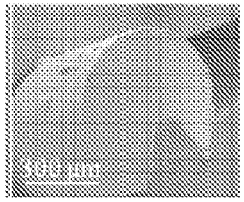
FIG. 3B shows a SEM image of a cross section of the side window without the buffer and cladding layers of the optical fiber.

The fabrication process in this example comprised of fixing and positioning a 10 cm multimode glass optical fiber (BFL48-400, buffer diameter: Tefzel, 730 µm; cladding diameter: hard polymer, 630 µm; core diameter: pure silica, 400 µm, 0.48 NA, Thorlabs) onto an acrylic substrate (30.48×60.96 cm). The substrate dimension was the same as the operation chamber of the laser micromachining system. The laser system used in this example was a commercially available VLS 3.50 laser platform with the fundamental wavelength of 10.6 µm and maximum power of 50 W. The laser was operated in a CW mode with power and scanning speed controlled through a computer. Throughout the fabrication process, the fiber samples remained stationary while the laser beam scanned point by point along the fiber axis using a gold mirror system in the delivery optics to guide its position. Upon irradiation with high enough laser power, phase transformation occurred inside the fiber core. With silica-based materials like the optical fiber's core, melting phase takes place at the heat-affected zone when the irradiance is ~$10^5$ W/cm$^2$. With an increase in the irradiation time, the melting material penetrates deep into the bulk. This step is called photoablation, which involves a precise removal of glass material and the introduction of a permanent structure change in the fiber core. By micromachining with a 50 W laser, a ~260 µm wide and ~135 µm crater-shaped side window was created with the 2 outer layers completely removed and the core partly removed, as shown in FIG. 3A and FIG. 3B. FIG. 3A shows a SEM image of a top view of a light window fabricated by a 50 W CW laser with buffer and cladding layer intact. FIG. 3B shows a SEM image of a cross section of the side window without the buffer and cladding layers.

Figure 4A:
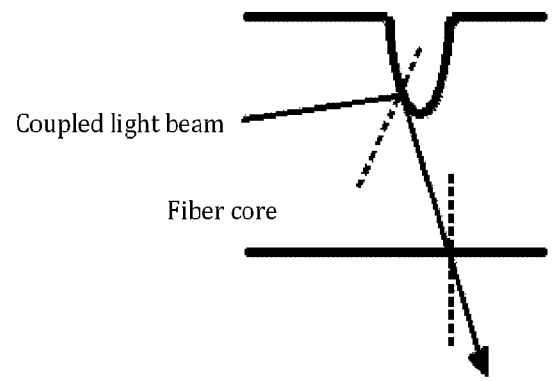
FIG. 4A shows a diagram of how the angle of the crater-shaped window frustrates the TIR condition of the coupled light in the fiber core and causes the light beam to be reflected to the side of the fiber.
Figure 4B:
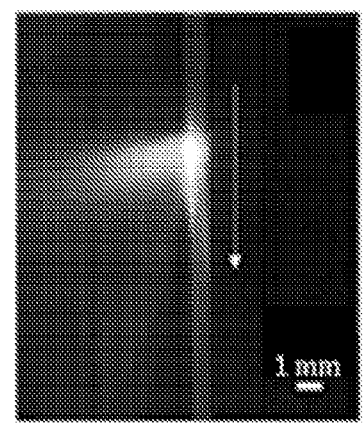
FIG. 4B shows a side-firing beam profile in acridine orange solution.

The angle of the crater shaped window caused the light beams travelling through the fiber core to reflect at the window interface. This was made possible because their incident angle is larger than the angle of total internal reflection (critical angle) between the glass and air interface; hence, a portion of coupled light inside the fiber core could be emitted through the side of the fiber (FIG. 4A). FIG. 4A shows how the angle of the crater-shaped window frustrated the TIR condition of the coupled light in the fiber core and caused the light beam to be reflected to the side of the fiber. However, for medical applications, it is more important to test the side-firing condition in an aqueous medium, as in the urethra. A fiber section with one side window was immersed in acridine orange solution; the other end was inserted into a multimode fiber connector (B10440A, Thorlabs). The connector was then attached and locked into a bare fiber terminator (BFT1, Thorlabs) mounted on a metallic stage. A 473 nm laser (Mai Tai HP, Spectra-Physics) was focused through a convex lens (f: 50 mm) into the fiber core. With this setup, the optical coupling efficiency of ~80% was easily achieved. Transmission loss of optical fiber was negligible. The side-firing light from the window excited the dye and gave green light emission with an angle of ~80° as shown in FIG. 4B. In FIG. 4B, the white arrow indicates the propagating direction of laser light inside the fiber core.

Figure 4C:
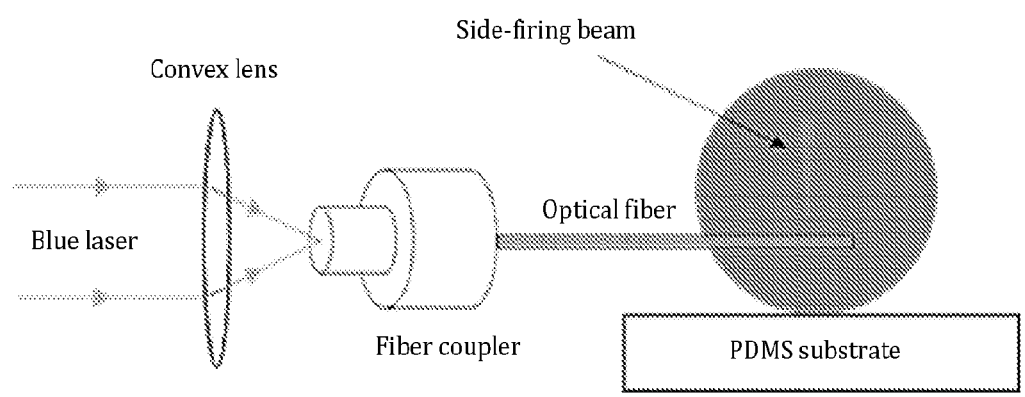
FIG. 4C shows a diagram of an optical setup used to take fluorescent profile images of side-firing light from the light window.
Figure 4D:
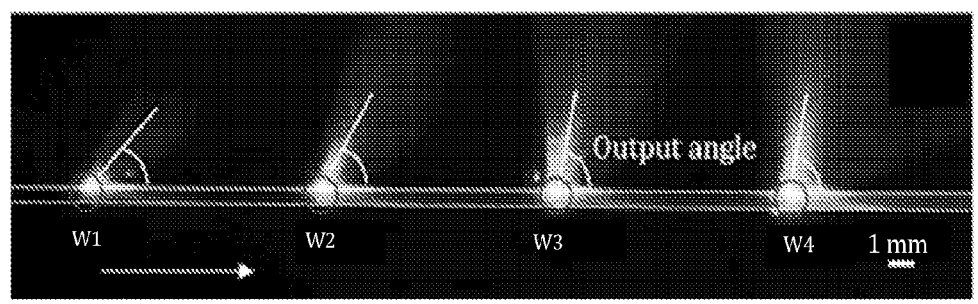
FIG. 4D shows a fluorescent profile of side-firing light from 4 windows in an optical fiber sample in acridine orange solution.

The side-firing angle can be controlled by adjusting the geometry of the side window with different $CO_2$ laser power (FIG. 5). The fluorescent profiles of a 4-window optical fiber sample were measured in acridine orange solution. Four windows: W1, W2, W3, W4 were cut with the laser power of 20 W, 30 W, 40 W, and 50 W respectively. The fiber sample was coupled with the blue laser. FIG. 4C shows the optical setup used to take fluorescent profile image of side-firing light from the light window. FIG. 4D shows the fluorescent profile of side-firing light from 4 windows optical fiber sample in acridine orange solution. Continuous white lines were added to highlight the optical fiber profile. Circles show the position of each window on the optical fiber sample. The white arrow indicates the direction of propagating laser inside the fiber core. The distance between each window is ~0.8 cm. The angle of the side window significantly affected the output light angle when cutting with the laser power of 20 to 30 W. The output angle for W1 was calculated as ~46° and W2 as ~59°. From 40-50 W, there was no significant difference in output angle. Both windows W3 and W4 had the output angle of ~80° (FIG. 4D). Cross sections of the fiber core after being cut with different laser powers are shown in FIG. 6. The window increased in both width and depth when cut with increasing laser power. FIG. 6A shows a cross section after cutting with laser power of 10 W, showing no visible change on the fiber core. FIG. 6B shows the results after cutting at 20 W. A small dent appears on the core (circled). FIG. 6C shows results after cutting at 30 W, showing that the laser started ablating a large portion of the core. FIG. 6D shows a deeper window at 40 W processing $CO_2$ laser.

Figure 7:
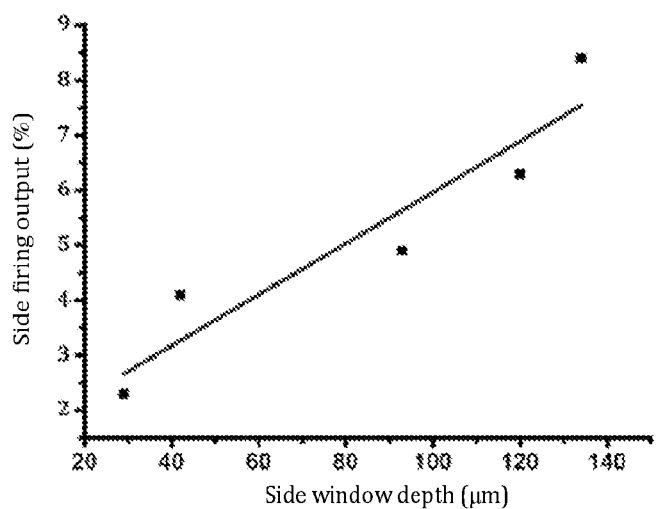
FIG. 7 shows side-firing light output from side windows as a function of side window depth in the optical fiber.

The power of side-firing light was measured by a handheld laser power meter (Ophir 7Z01500) with a photodiode sensor. It was shown that a single side window fabricated by 50 mW CW laser could fire more than ~8% of total coupled light inside the fiber core. Output light power was directly proportional to the depth of the window (FIG. 7), due to more incoming light beams interacting with the angled interface of the window and surrounding medium. Controlling the depth of the side window was made possible by tuning the power of the fabricating CW laser. Shooting the CW laser on the fiber multiple times can create deeper windows that can fire light up to 20% of total coupled light, but significantly reduce the fiber's strength. Depending on the applications, the depth of the side windows can be optimized to avoid breakage.

Figure 8A:
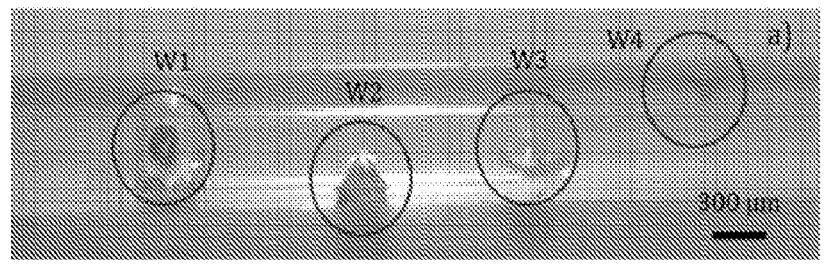
FIG. 8A shows four windows W1, W2, W3, and W4 (circles) positioned along the fiber axis with different orientation.
Figure 8B:
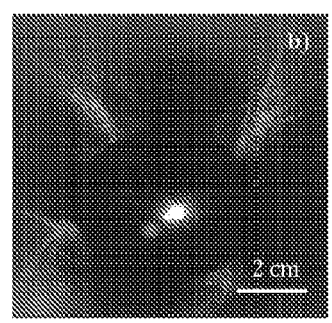
FIG. 8B shows 3-Dimensional light firing configuration from the 4 windows of FIG. 6A.

By simply rotating the optical fiber sample on the acrylic substrate, multiple windows could be placed in closed distance in different radial direction along the fiber axis, resulting in a 3D side emitting light configuration (FIG. 8); this allows the possibility to send pattern light using just one single fiber. FIG. 8A shows four windows W1, W2, W3, and W4 (circles) positioned along the fiber axis with different orientation, 90° difference. FIG. 8B shows 3-Dimensional light firing configuration from 4 windows. The optical fiber sample was coupled with HeNe laser and placed inside cone-shaped tube for beam profile imaging.

Example 2

In the previous example, for ease of demonstration, large multimode optical fibers were used. However, in medical applications, smaller size optical fiber is essential. It allows smooth inserting into the tissue, thus tissue damage is significantly reduced. The laser micromachining method can easily be scaled down depending on the type of the processing laser. With CW $CO_2$ laser, it suffers from the large heat-affected zone, hence for the VLS 3.50 laser platform, it could not be used on optical fiber smaller than 300 µm in diameter. To fabricate a side window on small optical fiber, a femtosecond (fs) laser was employed. A 100 fs laser pulse (820 nm) with a repetition rate of 80 MHz from a Ti-Sapphire laser system (Mai Tai HP, Spectra-Physics) was focused on the surface of the sample through an objective lens (60×, 0.75 NA). Optical fibers (Polymicro Technologies, FVP050055065) having 50 µm silica core with a high concentration of hydroxyl (OH) group, 2.5 µm doped silica cladding and 5 µm polyimide buffer jacket were used for fabricating side windows. At a high repetition rate of 80 MHz, the time interval between each successive laser pulse was far shorter than the time scale for heat diffusion out of focal volume (1 µs). Thereby, energy deposited by each laser pulse is more than it can diffuse away, thus raising the temperature of the material in the focal region and ultimately melting the surrounding material. By focusing the laser beam to a very small spot through an objective lens, sub-micron features can be made.

Figure 9A:
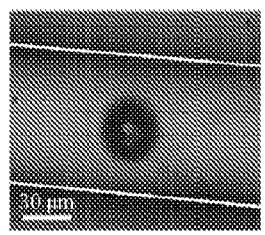
FIG. 9A shows a 5 μm opening hole on a buffer layer of a 65 μm fiber to expose the silica cladding.
Figure 9B:
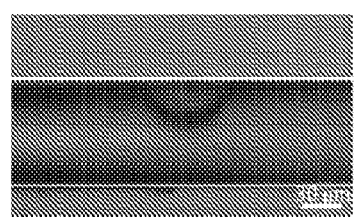
FIG. 9B shows a crater-shaped window created by buffer HF etching through the hole.
Figure 9C:
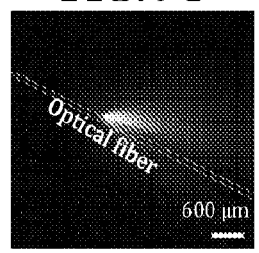
FIG. 9C shows a wide spread side-firing beam profile from the side window after buffer HF etching.
Figure 9D:
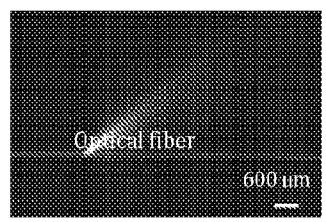
FIG. 9D shows a narrow side-firing beam profile from the side window after gold coating.

The laser pulse energy was adjusted to ~0.5 nJ to cut a circular shaped hole of 5 µm on the buffer layer, which exposed the silica cladding. Then, the fiber sample was immersed in buffer HF bath to etch the cladding and the core. Etch rate for cladding layer and the core was ~83 nm/min and ~73 nm/min respectively. As a result, a crater-shaped side window was formed (FIG. 9A). FIG. 9A shows a 5 µm opening hole on the buffer layer of 65 µm fiber to expose the silica cladding. FIG. 9B shows a crater-shaped window created by buffer HF etching through the hole. FIG. 9C shows a wide spread side-firing beam profile from the side window after buffer HF etching, and FIG. 9D shows a narrow side-firing beam profile from the side window after gold coating. Fiber samples were coupled with green laser light and immersed in R6G solution.

A low energy laser pulse and chemical etching was used in order to minimize the damage caused on the buffer layer. Using a high energy laser pulse would result in the surrounding buffer layer completely destroyed. Without this protective layer, the processing section was very brittle. Light firing efficiency of one single window on 65 µm optical fiber can be up to ~25% of total coupled light, due to higher light intensity for a small fiber. HF etching created a rough angled interface for the side window, thus, increasing the scattering of the reflected beams. As a result, side-firing beam profile on 65 µm fiber had a wide spread angle (FIG. 9B). In order to have more local light delivery, the opening side of the window was coated with gold by sputtering method, thus helping to narrow down the side-firing beam profile (FIG. 9C). This reduces the power of the output light significantly, but could still be sufficient for certain applications.

Example 3

Figure 10A:
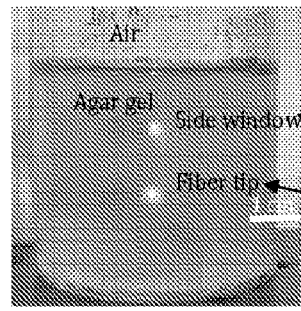
FIG. 10A shows a side view of an emission image of a 65 μm side-firing optical fiber in agar based tissue mimicking material.
Figure 10B:
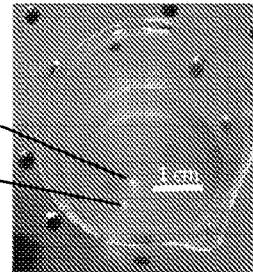
FIG. 10B shows a top view of an emission image of a 65 μm side-firing optical fiber in agar based tissue mimicking material.

The feasibility of the multipoint side-firing optical fiber in biomedical applications was confirmed. Multipoint side-firing capability of the fiber was investigated in agar based tissue mimicking material (0.5% w/v in water). Even though the fiber was immersed in a high refractive index medium (n=1.334), which could interrupt TIR condition at the side window, interface light was still observed firing out from the fiber side as shown in FIG. 10. FIG. 10 shows an emission image of 65 µm side-firing optical fiber in agar based tissue mimicking material from a side view (FIG. 10A) and a top view (FIG. 10B). This means the angle of the side window was sufficient enough to retain TIR condition of the laser beam at the window interface. There was no need for the encapsulation process of the firing sites as in predecessor devices. Furthermore, this experiment was also used to test the side-firing fiber strength in order to optimize the side window's depth. The obtained results showed that with the side window's depth of more than ½ of the fiber core's diameter, the fibers were more prone to break during an insertion test compared to a shallower window.

Example 4

Figure 11:
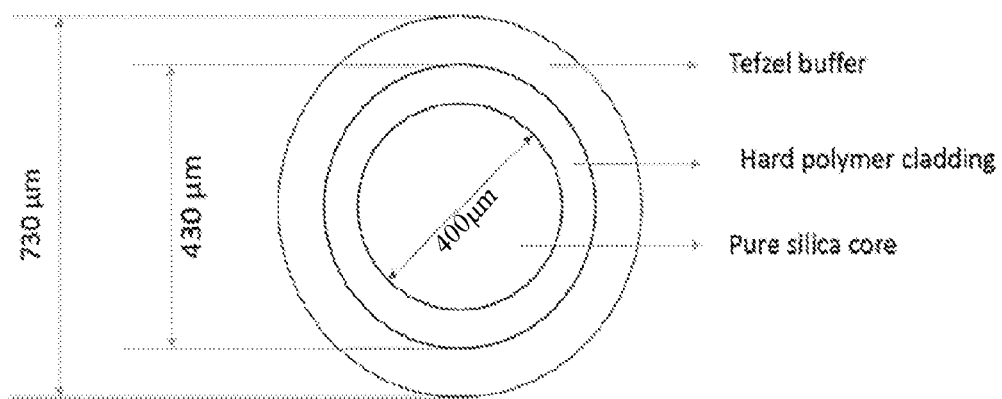
FIG. 11 shows a diagram of a cross section of an exemplary optical fiber used in embodiments of the present disclosure.

The laser cutter tool used in this example is Universal Laser System VLS 3.50, which can produce a single laser beam with maximum power of 50 W. The fiber chosen for the experiment was a silica/polymer fiber (Thorlabs BFL48-400). The fiber had core diameter of 400 µm and a numerical aperture of 0.48, as shown in FIG. 11. To cut open the fiber optic, first, a cut with desired length was introduced on a glass slide (75×50 mm), which acted as a cutting board for the fiber sample. Then, a 5 cm fiber optic sample was placed directly on top of the cut mark on the glass slide, and the laser was rerun to introduce the same cut on the fiber. Laser power was tuned to 3%, speed of 20%, and DPI of 1000. The fiber sample was cut multiple times on the same area in order not to cut too deep into the fiber core, otherwise, the fiber could be destroyed.

Figure 12:
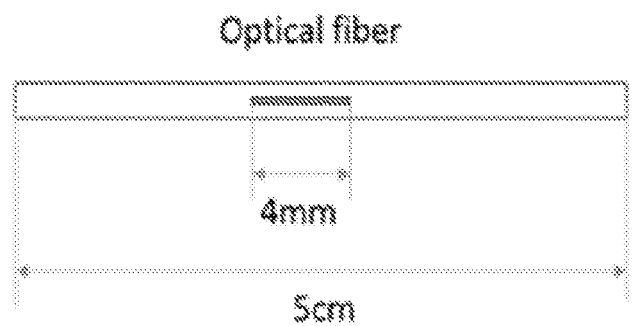
FIG. 12 shows a diagram of an optical fiber sample having a cut window in an embodiment of the present disclosure.

To prove the efficiency of the laser cutter in opening a window on the optical fiber, two methods were applied. In the first method, the cut window was immersed in a higher refractive index environment than the fiber core. If the window was free of jacket and cladding, total internal reflection at that part would be eliminated, and light would leak out. For this method, optical fiber samples were cut using a laser to open a small window on one side of the fiber, where the length of the cut window was 4 mm, as shown in FIG. 12. White light was projected into the fiber using a white light source and an objective lens.

A drop of immersion oil with refractive index of 1.54 was put on top the cut area of optical fiber. When white light was projected through the fiber, at the cut window cover with oil, because the refractive index of oil is higher than the silica core (~1.46), there was no total reflection at that part, thus light came out and laminated the drop of oil. This means that at the cut area of the optical fiber, the jacket and cladding surround the silica core had been completely removed. Therefore, immersion oil with higher refractive index was in contact with the silica core and terminated the total reflection effect of the optical fiber, creating a window for light to come out.

Figure 13:
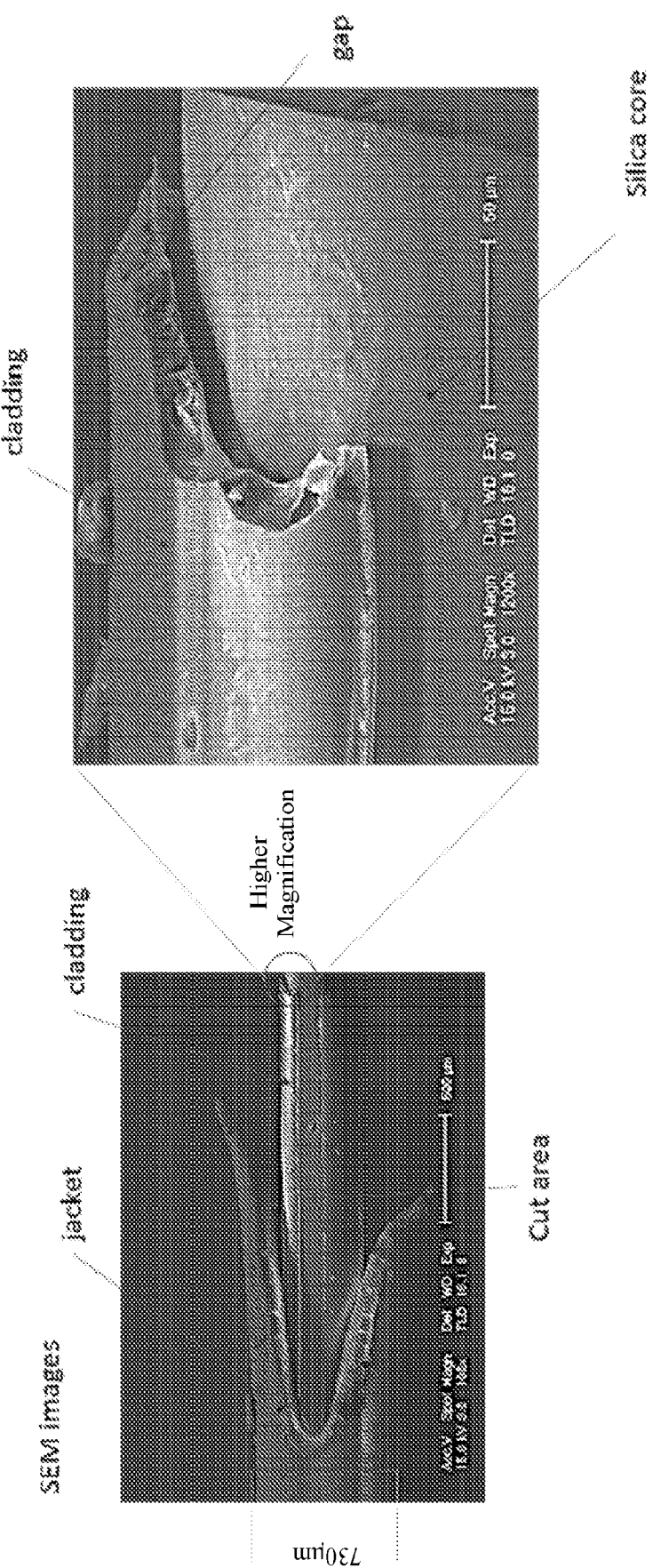
FIG. 13 shows a SEM image of a cut window on an optical fiber after etching with buffer HF solution.

For the second method, buffer hydrofluoric (HF) etching was applied due to the fact that HF can corrode silica. Therefore, if at the cut window, there is no polymer jacket or cladding layer to protect the fiber's silica core, effect of HF etching on the core can be seen with SEM image of the fiber sample. Sample preparation for this method was the same as the first method, except that, after finish cutting the window on the fiber optic using the laser, the remaining jacket layer at the window part was removed completely by a physical method in order for buffer HF solution to get into contact with the cut area. The fiber optic sample was dipped into buffer HF solution for 1 hours. After etching, optical samples were rinsed several times with excess water, ethanol, dried out, and coated with gold alloy for SEM imaging. For the sample before etching with buffer HF, using SEM image, it was easy to see that the cladding layer and the silica core of the fiber were adhered closely to each other. There was no gap between them. However, after etching with buffer HF, a gap appeared between the cladding layer and the silica core. FIG. 13 shows the SEM images after etching. This is a demonstration that the silica core of the fiber optic had been etched by the buffer HF solution, which meant that at the cut window, it was free from cladding. The SEM image also showed that the surface of the silica core exposed by the laser is smooth, and ready for deposition of SPR materials without any further polishing.

Figure 14:
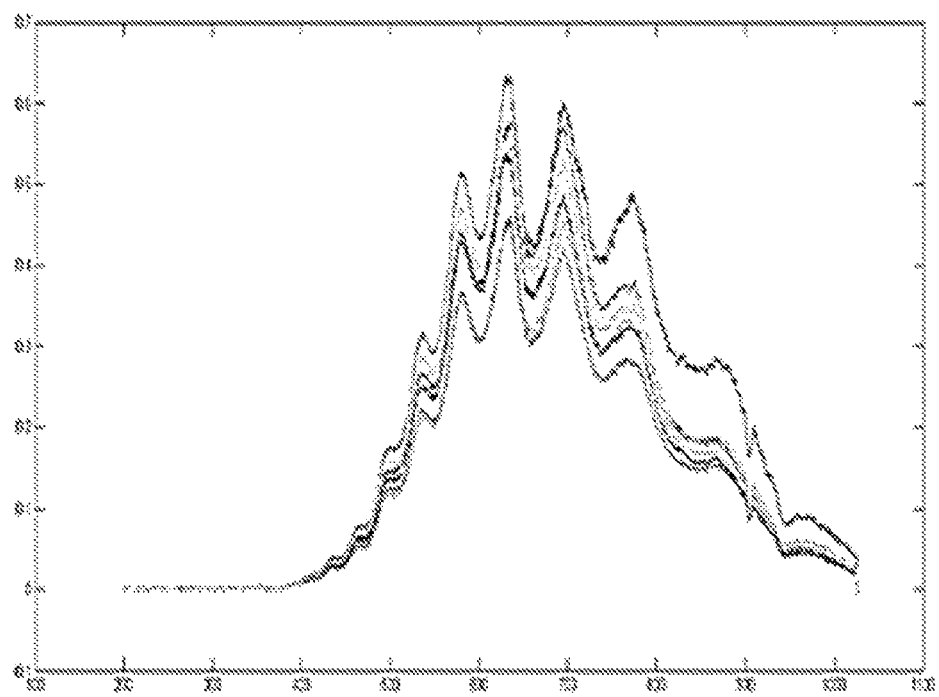
FIG. 14 shows output light spectra of seven measurements taken on an intact optical fiber at the same marked position.

Further analysis was done to quantify the amount of light leaked out from the window open on fiber optic sample. White light was generated using an optic illuminator, and focused through a 20× objective lens to couple white light into 400 μm core optical fiber. Intensity of light was measured using mini spectrometer. A fiber sample was fixed onto a holder with a trend in the middle to keep the fiber straight and stable when coupling light. Because of the high sensitivity of the spectroscopy to the position of output light from the optical fiber sample, with a very small change in position, a significant difference was seen in the resulting spectrum. Therefore, in order to get more consistent results in each measurement, the optical fiber sample was marked on one side using a scalpel to have a better control in the position of fiber in respect to the sensor of spectrometer. However, even with this set up, the obtained spectrum were still very inconsistent, and largely different to each other, as shown in FIG. 14.

Figure 15:
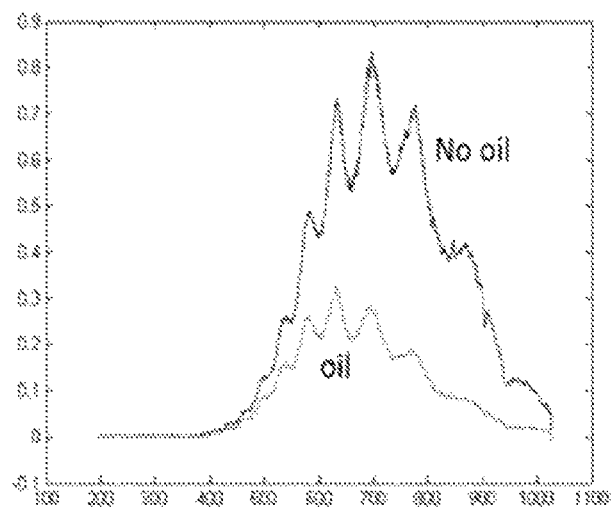
FIG. 15 shows change in output light intensity from an optical fiber having an open cut window with and without immersion oil dropped onto the cut area.

By calculating directly the percentage of intensity of leaked light from the output light's intensity of a cut optical fiber with and without immersion oil, the obtained results were much more consistent. Experiments were done on only one 5 cm optical fiber sample. The sample was opened with a 4 mm long window along sample length. The sample side with the window was placed face up on the sample holder, and the output light's intensity was measured. After that, a drop of immersion oil was put on the cut area, the fiber sample was kept in the same position, and the output light's intensity was measured again. With this setup, the dependence of light's intensity on fiber position could be minimized. The resulting spectrum showed a big difference in intensity of output light from optical fiber sample with and without immersion oil, shown in FIG. 15. The experiment was repeated 7 times, with data shown below in Table 1, and the percentage of leaked light was calculated to be ~69.18±3.63%.

TABLE 1

| No. | No oil | Oil | leaked intensity (%) |
|---|---|---|---|
| 1 | 733.249 | 195.2203 | 73.37598824 |
| 2 | 952.1152 | 245.9237 | 74.17080412 |
| 3 | 942.9142 | 329.7099 | 65.03288422 |
| 4 | 645.6019 | 209.9247 | 67.48387822 |
| 5 | 669.5326 | 203.6257 | 69.58688793 |
| 6 | 900.9885 | 275.3802 | 69.43576971 |
| 7 | 598.5325 | 208.4664 | 65.17041263 |
| | | Average | 69.17951787 |
| | | STD | 3.626237871 |

Figure 16A:
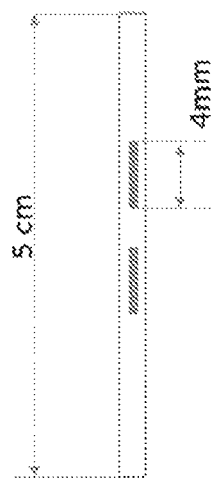
FIG. 16A shows a diagram of an optical fiber sample prepared to have two side windows.
Figure 16B:
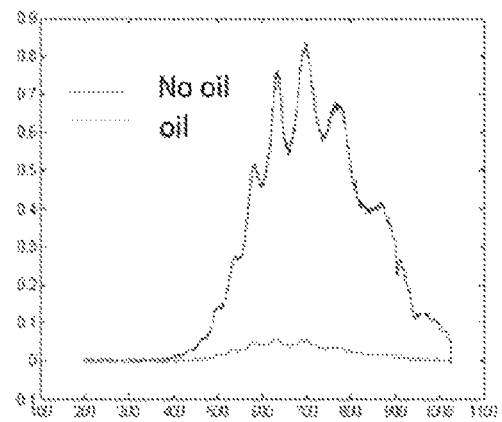
FIG. 16B shows change in output light intensity of an optical fiber having two open side windows with and without immersion oil dropped onto the cut area.

Using the same sample, another 4 mm window was cut on the same side of the optical fiber as the first window, as shown in FIG. 16A. The experiment above was repeated to demonstrate the effect of open multiple windows on optical fiber sample. The change in intensity was even more significant than with only one window, as shown in FIG. 16B. The experiment was also repeated 7 times, with data shown below in Table 2, and the percentage of leaked light was calculated to be ~83.47±5.63%.

TABLE 2

| No. | No oil | Oil | leaked intensity (%) |
|---|---|---|---|
| 1 | 738.0794 | 129.7045 | 82.42675517 |
| 2 | 614.3526 | 123.2251 | 79.94228396 |
| 3 | 538.6493 | 100.6401 | 81.31621075 |
| 4 | 783.66 | 129.4116 | 83.48625352 |
| 5 | 587.1613 | 140.0556 | 76.14699743 |
| 6 | 501.3394 | 63.5023 | 87.3334711 |
| 7 | 956.8856 | 60.926 | 93.63288569 |
| | | Average | 83.46926537 |
| | | STD | 5.62745102 |

The results showed the total amount of light intensity that escaped from the cut windows, but couldn't give exactly how much light leaked out from each individual window. For this, the mini-spectrometer can't be used, due to the small size of its detector which make it difficult to fix it in desired place for measurement. Furthermore, because the window size is much bigger than the detector, the results will not reflect the total intensity of leaked light. For this reason, instead of mini-spectrometer, a power meter with a silicon detector was used. Because the power meter can only detect one single wavelength, based on the light spectrum obtained above, the detected wavelength was set to 698 nm because of its highest intensity, and the average reading time of 10 s was used. A fiber optic sample was prepared differently compare to previous experiments. A 10 cm fiber sample was prepared with 4 different sized windows (4 mm, 3 mm, 1 mm, and 0.5 mm long, respectively) along the fiber length. Different size windows were also used to characterize the dependence of leaked light on the size of the window. The windows were then coated with PMMA, which has a higher refractive index than the silica core, by drop coating deposition method. With the PMMA layer on top of the windows, the detector of the power meter can be put closely to the exposed core, thus the power reading will be more exact.

Reading of power was repeated 6 times and averaged for comparison between each individual window. Data is shown below in Table 3, which indicated a decrease in power from the biggest window to the smallest window, which is in agreement with the conclusion that the bigger the window size, the more light will leak out.

TABLE 3

| Window size | Average power |
|---|---|
| 4 mm | 3.97 µW |
| 3 mm | 0.84 µW |
| 1 mm | 0.315 µW |
| 0.5 mm | 60.44 nW |

Figure 17:
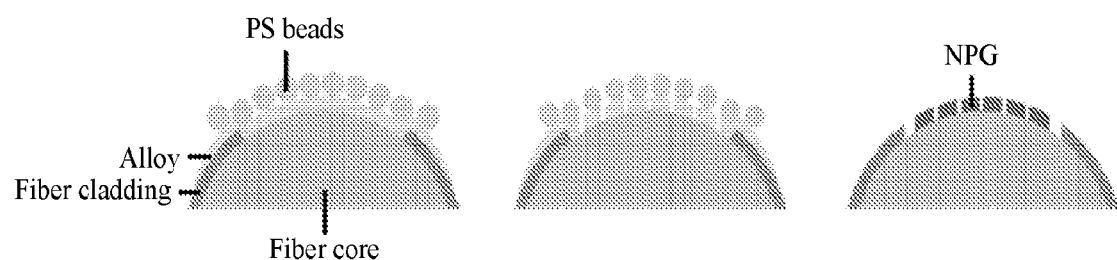
FIG. 17 shows a schematic diagram of a fabrication process for nanoporous gold discs (NPGD) on an optical fiber having an open cut window.
Figure 18:
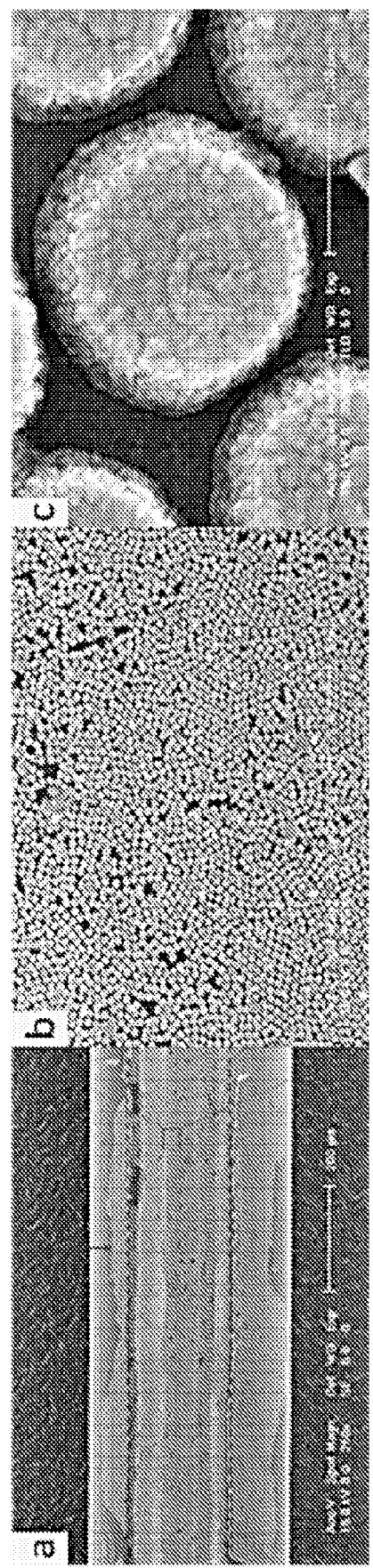
FIG. 18 shows scanning electron microscope (SEM) images showing NPGD fabricated on an optical fiber having an open cut window at (a) low, (b) intermediate, and (c) high resolution.

With the fiber precisely placed with the window facing up and fix onto a rigid substrate by tape, the fabrication of NPGD samples was carried following the previously described fabrication process. The process with a modified fiber structure is outlined in FIG. 17. The NPGD can cover the entire window, which ensures the strong interaction between the light and the plasmonic structure. SEM images were taken after the fabrication was done and the fiber was coated with 20 nm Au, as shown in FIG. 18. FIG. 18 shows in (a) the overall image of the optical fiber, with the boundary between the cladding and the core depicted by dashed lines. Zoomed-in images (see (b) and (c)) show high coverage and structural integrity of the NPGDs. The porous structures are not visible in these images because they are fully covered by 20 nm Au film.

This example demonstrates that laser cutting is an efficient method for opening small window(s) on optical fibers. The windows can be controlled in different sizes exactly, leading to the ability to fabricate multiple SPR sensor on the same fiber. With physical methods to expose the core of the fiber, at the cut area the fiber becomes very fragile, and can be broken with just a very little force. However, in accordance with the present methods, depending on the length of the fiber optic sample, the strength and flexibility of the fiber can still be kept for a certain degree, which is a benefit for remote sensing applications. The NPGD fabrication processes are carried out on these window opened fibers. SEM images show high NPGD coverage in the window, which ensures strong interaction between light and the plasmonic structure.

REFERENCES

The following documents and publications are hereby incorporated by reference.

J. Spigulis, J. Lazdins, D. Pfafrods, and M. Stafeckis, Med. Biol. Eng. Comput. 34, 285-286 (1996).
C. F. B. van Swol, R. M. Verdaasdonk, R. J. van Vliet, D. G. Molenaar, T. A. Boon, World J. Urol 13, 88-93 (1995).
U. Utzinger and R. R. Richards-Kortum, J. Biomed. Opt. 8(1), 121-147 (2003).
C. Kim, H. Park, and H. Lee, Lasers Surg. Med. 45(7), 437-449 (2013).
Seung H. L., Yong-Tak R., Dong H. S., Seongmook J., Youngwoong K., Seongmin J., Bok H. K., Won-Taek H., Opt. Express 23, 21254-21263 (2015).
Ik-Bu S., Youngseop K., Young-Chul N., In W. L., Jun K. K., Ho L., Opt. Express 18, 19755-19760 (2010).
Ofer S., Ken K., Nicholas D. O., Ayman F. A., Gilles B., Jean F. V., Alejandro R., Mihai I., John D. J., Yoel F., Opt. Express 14, 3929-3925 (2006).
Side glowing fiber, available at: www.somta.1v/wp30.htm
S. T. Lin, J. C. Wolfe, J. A. Dani, W. C. Shih, Opt. Lett. 37, 1-3 (2012).
S. T. Lin; M. Gheewala; J. A. Dani; J. C. Wolfe; W. C. Shih, Proc. SPIE 8565, Photonic Therapeutics and Diagnostics IX, 85655Y, 2013.
H. S. Carslaw, J. C. Jaeger, Conduction of Heat in Solids, Oxford University, 256 (1959).
Margaret L. Byron, Evan A. Variano, Exp Fluids 54, 1456 (2013).
N. Zorzos, E. S. Boyden, C. G. Fonstad, Opt. Lett. 35, 4133-4135 (2010).

What is claimed is:

1. A method for fabricating a multiple side-window side-firing optical fiber, comprising:
    (a) positioning an optical fiber in a fixed position, wherein the optical fiber is comprised of an inner silica core, an intermediate cladding layer, and an outer buffer layer having outer side walls;
    (b) directing a laser beam from a laser at a selected location on the outer side walls of the optical fiber at which a side window is intended to be placed, wherein the laser beam contacts the optical fiber for a selected period of irradiation time;
    (c) producing a crater-shaped side window in the optical fiber using the laser beam, wherein the crater-shaped side window penetrates through the outer buffer layer, the intermediate cladding layer, and at least partially into the inner silica core;
    (d) repositioning the optical fiber in an additional fixed position;
    (e) directing a laser beam from the laser at an additional selected location on the outer side walls of the optical fiber at which an additional side window is intended to be placed, wherein the laser beam contacts the optical fiber for an additional selected period of irradiation time;
    (f) producing an additional crater-shaped side window in the optical fiber using the laser beam, wherein the additional crater-shaped side window penetrates through the outer buffer layer, the intermediate cladding layer, and at least partially into the inner silica core; and
    (g) repeating steps (d), (e), and (f) a desired number of times to produce a desired number of additional side windows in the optical fiber.

2. The method of claim 1, wherein the laser is a continuous wave $CO_2$ laser.

3. The method of claim 1, wherein steps (b) and (e) further comprise adjusting power of the laser and the irradiation time to generate a desired depth of the crater-shaped side window and additional crater-shaped side window, wherein the depth is directly proportional to the power of the laser and the irradiation time.

4. The method of claim 3, wherein the power of the laser ranges from about 10 W to about 100 W.

5. The method of claim 3, wherein the depth of the crater-shaped side windows ranges from about 1 micron to about 300 microns.

6. The method of claim 1, wherein the optical fiber has a diameter of about 30 microns to about 1000 microns.

7. The method of claim 1, further comprising the step of applying an additional thin film coating to one or more of the crater-shaped side windows.

8. The multiple side-window side-firing optical fiber prepared by the method of claim 1.

9. A method for providing multiple simultaneous points of light to a region using a single optical fiber, comprising:
    fabricating a multiple side-window side-firing optical fiber according to claim 1;

inserting the multiple side-window side-firing optical fiber into the region; and directing a laser through the multiple side-window side-firing optical fiber, whereby laser light passes through the distal end of the fiber, and whereby laser light passes through the outer side walls of the fiber at locations opposite the crater-shaped side windows.

10. A method for fabricating a surface plasmon resonance (SPR)-based or localized surface plasmon resonance (LSPR)-based fiber optic sensor, comprising:

fabricating a multiple side-window side-firing optical fiber according to claim 1; and depositing a layer of gold or silver on at least one of the crater-shaped windows of the multiple side-window side-firing optical fiber to produce a surface plasmon resonance (SPR)-based or localized surface plasmon resonance (LSPR)-based fiber optic sensor.

11. The method of claim 10, wherein the layer of gold or silver comprises a thin film of gold or silver, a layer of gold or silver nanoparticles, or combinations thereof.

12. The method of claim 11, wherein the gold or silver nanoparticles are nanoporous gold discs.

13. A method for fabricating a multiple side-window side-firing optical fiber, comprising:

(a) positioning an optical fiber in a fixed position, wherein the optical fiber has a distal end and is comprised of an inner silica core, an intermediate cladding layer, and an outer buffer layer having outer side walls;

(b) directing a laser beam from a laser at a selected location on the outer side walls of the optical fiber at which a side window is intended to be placed, wherein the laser beam contacts the optical fiber for a selected period of irradiation time;

(c) producing a circular-shaped opening at the selected location in the optical fiber using the laser beam, wherein the circular-shaped opening penetrates through the outer buffer layer without penetrating the intermediate cladding layer or the inner silica core;

(d) immersing at least a portion of the optical fiber including the circular-shaped opening in a chemical etching solution, wherein the chemical etching solution penetrates through the intermediate cladding layer and at least partially into the inner silica core of the optical fiber to create a crater-shaped side window at the selected location in the optical fiber;

(e) repositioning the optical fiber in an additional fixed position;

(f) directing a laser beam from the laser at an additional selected location on the outer side walls of the optical fiber at which an additional side window is intended to be placed, wherein the laser beam contacts the optical fiber for an additional selected period of irradiation time;

(g) producing an additional circular-shaped opening at the additional selected location in the optical fiber using the laser beam, wherein the additional circular-shaped opening penetrates through the outer buffer layer without penetrating the intermediate cladding layer or the inner silica core;

(h) immersing at least a portion of the optical fiber including the additional circular-shaped opening in a chemical etching solution, wherein the chemical etching solution penetrates through the intermediate cladding layer and at least partially into the inner silica core of the optical fiber to create an additional crater-shaped side window at the selected location in the optical fiber; and (i) repeating steps (e), (f), (g), and (h) a desired number of times to produce a desired number of additional side windows in the optical fiber.

14. The method of claim 13, wherein the laser is a pulsed femtosecond laser.

15. The method of claim 13, wherein steps (b) and (f) further comprise adjusting power of the laser and the irradiation time to generate a desired depth of the circular-shaped opening and the additional circular-shaped opening, wherein the depth is directly proportional to the power of the laser and the irradiation time.

16. The method of claim 15, wherein the power of the laser ranges from about 10 W to about 100 W.

17. The method of claim 15, wherein the depth of the crater-shaped side window ranges from about 1 micron to about 300 microns.

18. The method of claim 13, wherein the optical fiber has a diameter of about 30 microns to about 1000 microns.

19. The method of claim 13, wherein the chemical etching solution is buffered HF.

20. The method of claim 13, further comprising the step of applying an additional thin film coating to one or more of the crater-shaped side windows.

21. The multiple side-window side-firing optical fiber prepared by the method of claim 13.

22. A method for providing multiple simultaneous points of light to a region using a single optical fiber, comprising:

fabricating a multiple side-window side-firing optical fiber according to claim 12;

inserting the multiple side-window side-firing optical fiber into the region; and directing a laser through the multiple side-window side-firing optical fiber, whereby laser light passes through the distal end of the fiber, and whereby laser light passes through the outer side walls of the fiber at locations opposite the crater-shaped side windows.

23. The method of claim 22, wherein the region is located within a human or animal subject.

24. A method for fabricating a surface plasmon resonance (SPR)-based or localized surface plasmon resonance (LSPR)-based fiber optic sensor, comprising:

fabricating a multiple side-window side-firing optical fiber according to claim 12; and depositing a layer of gold or silver on at least one of the crater-shaped windows of the multiple side-window side-firing optical fiber to produce a surface plasmon resonance (SPR)-based or localized surface plasmon resonance (LSPR)-based fiber optic sensor.

25. The method of claim 24, wherein the layer of gold or silver comprises a thin film of gold or silver, a layer of gold or silver nanoparticles, or combinations thereof.

26. The method of claim 25, wherein the gold or silver nanoparticles are nanoporous gold discs.

* * * * *

UNITED STATES PATENT AND TRADEMARK OFFICE
CERTIFICATE OF CORRECTION

PATENT NO. : 11,124,449 B2
APPLICATION NO. : 16/326986
DATED : September 21, 2021
INVENTOR(S) : Wei-Chuan Shih It is certified that error appears in the above-identified patent and that said Letters Patent is hereby corrected as shown below:

In the Specification

In Column 1, Lines 10-15, delete "The present invention used in part funds from the National Institute of Health (NIH) (NIH 1R21NS084301-01A1), National Science Foundation (NSF) CAREER Award (CBET-1151154), and Department of Interior BSEE. The United States Government has certain rights in the invention.", and insert -- "This invention was made with government support under Award No. NIH 1R21NS084301-01A1 awarded by the National Institute of Health (NIH), and CAREER Award No. CBET-1151154 awarded by the National Science Foundation (NSF), and Department of Interior BSEE. The government has certain rights in the invention." --, therefor.

Signed and Sealed this
Second Day of April, 2024

Katherine Kelly Vidal
*Director of the United States Patent and Trademark Office*